United States Patent
Yamagishi et al.

(10) Patent No.: US 9,301,906 B2
(45) Date of Patent: Apr. 5, 2016

(54) DENTRIFICE COMPOSITION

(75) Inventors: Atsushi Yamagishi, Funabashi (JP); Sei Tsutsui, Yokohama (JP)

(73) Assignee: Kao Corporation, Tokyo (JP)

( * ) Notice: Subject to any disclaimer, the term of this patent is extended or adjusted under 35 U.S.C. 154(b) by 234 days.

(21) Appl. No.: 14/008,210

(22) PCT Filed: Apr. 6, 2011

(86) PCT No.: PCT/JP2011/058717
§ 371 (c)(1),
(2), (4) Date: Sep. 27, 2013

(87) PCT Pub. No.: WO2012/137325
PCT Pub. Date: Oct. 11, 2012

(65) Prior Publication Data
US 2014/0017179 A1    Jan. 16, 2014

(51) Int. Cl.
*A61K 8/21* (2006.01)
*A61K 8/34* (2006.01)
*A61K 8/60* (2006.01)
*A61Q 11/00* (2006.01)
*A61K 8/73* (2006.01)
*A61K 8/11* (2006.01)

(52) U.S. Cl.
CPC ... *A61K 8/21* (2013.01); *A61K 8/11* (2013.01); *A61K 8/345* (2013.01); *A61K 8/60* (2013.01); *A61K 8/73* (2013.01); *A61K 8/731* (2013.01); *A61K 8/733* (2013.01); *A61K 8/737* (2013.01); *A61Q 11/00* (2013.01)

(58) Field of Classification Search
USPC .......................................................... 424/52
See application file for complete search history.

(56) References Cited

U.S. PATENT DOCUMENTS

| | | | |
|---|---|---|---|
| 3,105,798 A * | 10/1963 | Holliday et al. | 424/52 |
| 3,970,747 A | 7/1976 | Barth | |
| 5,089,255 A | 2/1992 | Gaffar et al. | |
| 5,424,059 A | 6/1995 | Prencipe et al. | |
| 6,471,946 B1 | 10/2002 | Takatsuka et al. | |
| 2003/0170185 A1 | 9/2003 | Takatsuka et al. | |
| 2008/0279947 A1 | 11/2008 | Nowak et al. | |
| 2010/0124560 A1 | 5/2010 | Hugerth et al. | |

FOREIGN PATENT DOCUMENTS

| | | |
|---|---|---|
| CA | 1 250 807 A | 3/1989 |
| EP | 0 138 705 A2 | 4/1985 |
| EP | 1 072 253 A1 | 1/2001 |
| JP | 60-204709 A | 10/1985 |
| JP | 3-48613 A | 3/1991 |
| JP | 06-122616 A | 5/1994 |
| JP | 06-122617 A | 5/1994 |
| JP | 10-155410 A | 6/1998 |
| JP | 11-012143 A | 1/1999 |
| JP | 11-049653 A | 2/1999 |
| JP | 2000-072638 A | 3/2000 |
| JP | 2000-247852 A | 9/2000 |
| JP | 2001-002540 A | 1/2001 |
| JP | 2001-002541 A | 1/2001 |
| JP | 2004-161719 A | 6/2004 |
| JP | 2004-210721 A | 7/2004 |
| JP | 2005-029484 A | 2/2005 |
| JP | 2009-023953 A | 2/2009 |
| JP | 2011-0456654 A | 3/2011 |
| JP | 2011-074066 A | 4/2011 |
| JP | 2012-219039 A | 11/2012 |

OTHER PUBLICATIONS

International Search Report (ISR) for PCT/JP2011/058717; I.A. fd: Apr. 6, 2011, mailed Jun. 10, 2011 from the Japanese Patent Office, Tokyo, Japan.
International Preliminary Report on Patentability (IPRP), Chapter I of the Patent Cooperation Treaty, including the Written Opinion for PCT/JP2011/058717; I.A. fd: Apr. 6, 2011, issued Oct. 8, 2013, by the International Bureau of WIPO, Geneva, Switzerland.
Takatsuka, T., "Effect of the toothpaste containing ISOMALT on remineralization," The Cell 37(3):100-103 (2005).
Extended European search report including the supplementary European search report and the European search opinion, for EP Patent Application No. 11863068.0, Sep. 3, 2014, European Patent Office, Munich Germany.

* cited by examiner

*Primary Examiner* — Walter Webb
(74) *Attorney, Agent, or Firm* — Sterne, Kessler, Goldstein & Fox P.L.L.C.

(57) ABSTRACT

Provided is a dentifrice composition which has excellent dental caries preventive effect by improving the uptake of fluoride ions into tooth enamel or dentin and improving acid resistance.

A dentifrice composition comprising the following components (A), (B), (C) and (D):
(A) from 0.002 to 5% by mass of a fluoride ion supplying compound in terms of fluorine,
(B) from 25 to 65% by mass of a sugar alcohol, which is dissolved in an amount of 5 to 30 g in 100 g of an aqueous solution at 20° C.,
(C) from 10 to 25% by mass of water, and
(D) from 0.1 to 1.2% by mass of a binder,
wherein the mass ratio of the component (B) to the component (C), the mass ratio (B/C), is more than 1 and 6 or less.

22 Claims, No Drawings

DENTRIFICE COMPOSITION

FIELD OF THE INVENTION

The present invention relates to a dentifrice composition containing a fluoride ion supplying compound.

BACKGROUND OF THE INVENTION

The main component of the tooth is hydroxyapatite. In the oral cavity, elution of phosphate ions and calcium ions (decalcification) and crystallization into calcium phosphate and hydroxyapatite (remineralization) are normally in equilibrium. Bacteria such as *Streptococcus mutans* decompose sucrose and the like to produce organic acids and lower pH. Because of that, calcium and the like of the teeth are eluted to promote decalcification, which leads to the progression of dental caries. In the initial stage of dental caries, the decalcified lesion beneath the surface of the tooth called as a white spot is formed in enamel. It is known that, at that stage, fluoride ions promote crystallization of calcium ions and phosphate ions, i.e., remineralization, to thereby enable prevention of dental caries and elimination of such white spot.

On the other hand, sugar alcohols such as xylitol are known to be nonfermentable and to have an action of suppressing growth of cariogenic bacteria. Patent Document 1 has reported a composition for oral cavity containing xylitol and a fluorine compound in a certain ratio. In addition, as a technique to promote remineralization by a fluorine compound, Patent Document 2 describes a composition for oral cavity containing a sugar alcohol such as xylitol, sodium fluoride and magnesium ions, and Patent Document 3 describes a composition for oral cavity containing Palatinit and a fluorine compound and shows the results that as the content of Palatinit increases, the amount of remineralization becomes large.

CITATION LIST

Patent Document

Patent Document 1: JP 3-48613 A
Patent Document 2: JP 11-12143 A
Patent Document 3: JP 2000-247852 A

SUMMARY OF THE INVENTION

The present invention provides the following inventions.

[1] A dentifrice composition comprising the following components (A), (B), (C) and (D):

(A) from 0.002 to 5% by mass of a fluoride ion supplying compound in terms of fluorine, (B) from 25 to 65% by mass of a sugar alcohol, which is dissolved in an amount of from 5 to 30 g per 100 g of an aqueous solution at 20° C., (C) from 10 to 25% by mass of water, and (D) from 0.1 to 1.2% by mass of a binder, wherein the mass ratio of the component (B) to the component (C), the mass ratio (B/C), is more than 1 and 6 or less.

Further, preferred embodiments of the present invention are as follows.

[2] The dentifrice composition as set forth in [1], wherein the viscosity (20° C.) of the composition is from 500 to 10000 dPa·s.

[3] The dentifrice composition as set forth in [1] or [2], wherein when diluting the composition by adding 25% by mass of water in the mass ratio, the viscosity is 10% or less of the viscosity before dilution.

[4] The dentifrice composition as set forth in any one of [1] to [3], wherein the fluoride ion supplying compound (A) is one or more selected from the group consisting of sodium fluoride and ammonium fluoride.

[5] The dentifrice composition as set forth in any one of [1] to [4], wherein the fluoride ion supplying compound (A) is sodium fluoride.

[6] The dentifrice composition as set forth in any one of [1] to [5], wherein the content of component (A) is from 0.05 to 1% by mass in terms of fluorine.

[7] The dentifrice composition as set forth in any one of [1] to [6], wherein the sugar alcohol (B) is one or more selected from the group consisting of mannitol, α-D-glucopyranosyl-1,6-sorbitol, α-D-glucopyranosyl-1,6-mannitol and reduced PALATINOSE™.

[8] The dentifrice composition as set forth in any one of [1] to [7], wherein the mass ratio of the component (B) to the component (C), the mass ratio (B/C), is from 1.2 to 3.

[9] The dentifrice composition as set forth in any one of [1] to [8], wherein the content of the component (B) is from 30 to 55% by mass and the mass ratio of the component (B) to the component (C), the mass ratio (B/C), is from 1.5 to 3.

[10] The dentifrice composition as set forth in any one of [1] to [9], wherein the content of the component (C) is from 10 to 20% by mass.

[11] The dentifrice composition as set forth in any one of [1] to [10], further comprising (E) glycerin in such an amount that the mass ratio to water (C), the mass ratio (E/C), is from 3/1 to 1/3.

[12] The dentifrice composition as set forth in any one of [1] to [11], wherein the binder (D) is one or more selected from the group consisting of sodium carboxymethyl cellulose, hydroxyethyl cellulose, carboxyvinyl polymer, xanthan gum, carrageenan, sodium alginate, hydroxypropyl cellulose and sodium chondroitin sulfate.

[13] The dentifrice composition as set forth in any one of [1] to [12], further comprising (F) a sugar alcohol having the solubility of more than 30 g in 100 g of an aqueous solution at 20° C., in such an amount that the mass ratio to (C) water, the mass ratio (F/C), is less than 1.

[14] The dentifrice composition as set forth in any one of [1] to [13], wherein the component (F) is one or more selected from the group consisting of erythritol, xylitol, maltitol and sorbitol.

[15] The dentifrice composition as set forth in any one of [1] to [14], wherein the mass ratio to the component (B) of (F1) sugar alcohol having the solubility of more than 30 g and 50 g or less in 100 g of an aqueous solution at 20° C., the mass ratio (F1/B), is 1 or less;

the mass ratio to the component (B) of (F2) sugar alcohol having the solubility of more than 50 g and 70 g or less in 100 g of an aqueous solution at 20° C., the mass ratio (F2/B), is 0.2 or less; and the mass ratio to the component (B) of (F3) sugar alcohol having the solubility of more than 70 g in 100 g of an aqueous solution at 20° C., the mass ratio (F3/B), is 0.1 or less.

[16] A method for promoting the uptake of fluorine into teeth, comprising applying the dentifrice composition as set forth in any one of [1] to [15] to the oral cavity.

[17] The dentifrice composition as set forth in any one of [1] to [15] for use in promoting the uptake of fluorine into teeth.

[18] Use of the dentifrice composition as set forth in any one of [1] to [15] for promoting the uptake of fluorine into teeth.

[19] Use of the dentifrice composition as set forth in any one of [1] to [15] for producing an agent for promoting the uptake of fluorine into teeth.

DETAILED DESCRIPTION OF THE INVENTION

Increasing the concentration of fluoride ions is considered as one method to uptake fluoride ions into tooth enamel and dentin and to promote remineralization. However, from viewpoints of solubility and safety of fluoride ions, it is difficult for a dentifrice composition to contain a large amount of fluoride ions, and it is desirable to efficiently uptake a small amount of fluoride ions into enamel and dentin. On the other hand, Patent Documents 2 and 3 describe that the dentifrice composition which contains a fluoride ion supplying compound and sugar alcohol in combination prevent dental caries by both effects of remineralization and growth suppression of cariogenic bacteria. However, the investigation by the present inventor indicated that the amount of fluoride ion uptake into tooth enamel and dentin was not necessarily large.

Accordingly, the present invention relates to a provision of a dentifrice composition having excellent dental caries preventive effect and also having remineralization effect by improving the uptake of fluoride ions into tooth enamel and dentin and improving acid resistance.

The present inventors made various investigations about the causes why the amount of fluoride ion uptake into tooth enamel and dentin was not sufficiently increased despite the use of fluoride ion supplying compounds and sugar alcohols in combination. As a result, it was unexpectedly revealed that when the water amount was too large relative to the amount of sugar alcohols, the amount of fluoride ion uptake into tooth enamel and the like was not sufficiently increased, even though a sufficient amount of sugar alcohols was dissolved. On the other hand, also when the water amount was too small, the amount of fluoride ion uptake into tooth enamel and the like was not increased sufficiently.

Further investigations found that by using a fluoride ion supplying compound and a sugar alcohol having low solubility in water in combination and by adjusting the water amount within a certain range, the amount of fluoride ion uptake into tooth enamel and dentin was remarkably improved and the acid resistance was improved, thereby being able to obtain a dentifrice composition having excellent dental caries preventive effect.

The use of a dentifrice composition of the present invention enables efficient uptake of fluoride ions of a fluoride ion supplying compound into tooth enamel and dentin and improves acid resistance, which improves dental caries preventive effect.

Hereinafter, the present invention will be described in detail.

The dentifrice composition of the present invention contains a fluoride ion supplying compound (A). The fluoride ion supplying compound (A) is a fluorine compound and means a compound which releases fluoride ions in an aqueous solution. The fluoride ion supplying compound may be either an inorganic compound or an organic compound. Specific examples thereof include sodium fluoride, potassium fluoride, tin fluoride, sodium silicon fluoride, ammonium fluoride, aluminum fluoride, silver fluoride, hexylamine hydrofluoride, decanolamine hydrofluoride, octadecenylamine hydrofluoride and the like. Sodium fluoride and ammonium fluoride are preferable and from a viewpoint that the amount of fluoride ion uptake into tooth enamel and the like is large, sodium fluoride is more preferable. One kind or a combination of two or more kinds of these fluoride ion supplying compounds may be contained in the dentifrice composition of the present invention. In addition, the dentifrice composition of the present invention may contain other fluorides such as sodium monofluorophosphate as a fluorine compound other than the fluoride ion supplying compound (A), which do not supply fluoride ion directly.

From viewpoints of ensuring the sufficient amount of fluoride ion uptake into tooth enamel and the like and safety, the composition contains from 0.002 to 5% by mass, more preferably from 0.01 to 1% by mass and even more preferably from 0.05 to 1% by mass of the fluoride ion supplying compound (A) in terms of fluoride ions.

The dentifrice composition of the present invention contains the sugar alcohol (B), which is dissolved in an amount of from 5 to 30 g in 100 g of an aqueous solution at 20° C. Examples of the sugar alcohol (B) which is dissolved in an amount of from 5 to 30 g in 100 g of an aqueous solution at 20° C., used in the present invention include mannitol, α-D-glucopyranosyl-1,6-sorbitol, α-D-glucopyranosyl-1,6-mannitol, reduced PALATINOSE™ which is a mixture of α-D-glucopyranosyl-1,6-sorbitol and α-D-glucopyranosyl-1,6-mannitol, and the like.

Mannitol is a kind of hexitol and a sugar alcohol of mannose. Mannitol is industrially produced by electroreduction of corn starch sugar and high pressure reduction of sucrose. Mannitol used in the present invention may be at least one kind selected from the group consisting of D-mannitol, L-mannitol and D, L-mannitol, and naturally-occurring D-mannitol is easily available and preferable, but is not especially limited thereto. The solubility of mannitol is 18 g in 100 g of an aqueous solution at 20° C.

Reduced PALATINOSE™ is a sugar alcohol of a disaccharide and is an equimolar mixture of α-D-glucopyranosyl-1,6-mannitol and its isomer, α-D-glucopyranosyl-1,6-sorbitol. Using sucrose as a raw material, reduced PALATINOSE™ is obtained by converting sucrose into PALATINOSE™ by glycosyltransferase followed by a hydrogenation reaction. In addition, reduced PALATINOSE™ has another name of isomalt and an example of the commercially available products is "PALATINIT"™ (product name) from Mitsui Sugar Co., Ltd. and Sudzucker AG Company (Japanese name: Nandoku Seitou). The solubility of PALATINIT™ is 28 g in 100 g of an aqueous solution at 20° C.

One kind or a mixture of two or more kinds of these sugar alcohols (B) may be used. In addition, either a powder form or a granular form of the sugar alcohol (B) may be used.

From a viewpoint of increasing the amount of fluoride ion uptake into tooth enamel and the like, the dentifrice composition of the present invention contains from 25 to 65% by mass, more preferably from 30 to 60% by mass and even more preferably from 30 to 55% by mass of these sugar alcohols (B).

From a viewpoint of increasing the amount of fluoride ions uptake into tooth enamel and the like, the content of water (C) in the dentifrice composition of the present invention is important and is from 10 to 25% by mass and more preferably from 10 to 20% by mass. It is believed that when from 10 to 25% by mass of water (C) is contained, the existence of an undissolved sugar alcohol (B) confers structural viscosity on the composition and the fluidity of a fluoride ion supplying compound dissolved in contained water (C) can be ensured. In addition, it is considered that since the dissolved amount of the sugar alcohol (B) in water is small, the concentration of a fluoride ion supplier in water (C) can be increased and the high-concentration fluoride ion supplier flows to come into contact with teeth. Thus, the dentifrice composition of the present invention can increase the amount of fluoride ion uptake into tooth enamel and the like. It should be noted that water (C) includes water contained in components such as a sorbitol solution in addition to purified water being mixed.

In the dentifrice composition of the present invention, preferably the mass ratio (B/C) (the mass ratio of the sugar alcohol (B) to water (C)) is more than 1 and 6 or less, the amount of the sugar alcohol (B) is larger than that of water (C), the sugar alcohol (B) is contained in the dentifrice composition exceeding the dissolved saturation level, and the undissolved sugar alcohol (B) exists. From a viewpoint of ensuring the fluidity of the fluoride ion supplying compound (A) dissolved in water (C) while conferring structural viscosity on the composition by the existence of the undissolved sugar alcohol (B), the mass ratio (B/C) (the mass ratio of the sugar alcohol (B) to water (C)) is further preferably from 1.2 to 4, more preferably from 1.2 to 3 and still further preferably from 1.5 to 3.

Although the dentifrice composition of the present invention contains the sugar alcohol (B) having the above-mentioned certain solubility, the dentifrice composition may further contain a different sugar alcohol (F) having the solubility of more than 30 g in 100 g of an aqueous solution at 20° C. As the different sugar alcohol (F), a sugar alcohol (F1) having the solubility of more than 30 g and 50 g or less, a sugar alcohol (F2) having the solubility of more than 50 g and 70 g or less and a sugar alcohol (F3) having the solubility of more than 70 g in 100 g of an aqueous solution at 20° C., may be contained. The different sugar alcohol (F) is preferably the sugar alcohol (F1) from a viewpoint of the amount of fluorine uptake into tooth enamel and the like.

When the different sugar alcohol (F) is contained, the mass ratio (F/C) (the mass ratio to water (C) contained in the dentifrice composition) is preferably less than 1, more preferably 0.75 or less and even more preferably 0.5 or less.

When the different sugar alcohol (F1) is contained, the mass ratio (F1/B) (the mass ratio to the sugar alcohol (B)) is preferably 1 or less, more preferably 0.8 or less and even more preferably 0.5 or less. When the sugar alcohol (F2) is contained, the mass ratio (F2/B) (the mass ratio to the sugar alcohol (B)) is preferably 0.2 or less, more preferably 0.18 or less and even more preferably 0.17 or less. When the sugar alcohol (F3) is contained, the mass ratio (F3/B) (the mass ratio to the sugar alcohol (B)) is preferably 0.1 or less and more preferably 0.05 or less.

Examples of the sugar alcohol (F1) include erythritol, the solubility of which is 36 g in 100 g of an aqueous solution at 20° C., and the like. Examples of the sugar alcohol (F2) include xylitol, the solubility of which is 66 g, maltitol, the solubility of which is 60 g in 100 g of an aqueous solution at 20° C. and the like. Examples of the sugar alcohol (F3) include sorbitol, the solubility of which is 72 g in 100 g of an aqueous solution at 20° C.

In addition, the dentifrice composition of the present invention preferably contains the binder (D). Examples of the binder (D) include sodium carboxy methylcellulose, hydroxyethyl cellulose, carboxyvinyl polymer, xanthan gum, carrageenan, sodium alginate, hydroxypropyl cellulose, sodium chondroitin sulfate and the like. Sodium carboxy methylcellulose, xanthan gum and carrageenan are more preferable. One kind or two or more kinds thereof may be used.

Generally, the binder (D) is added to a gelatinous dentifrice for gelation or to a paste dentifrice and a toothpaste for binding. In the present invention, from a viewpoint of ensuring the fluidity of fluoride ions in water (C), the dentifrice composition of the present invention contains preferably 0.1% by mass or more and 1.2% by mass or less, more preferably 1.0% by mass or less, even more preferably less than 1.0% by mass and even more preferably less than 0.8% by mass of the binder.

The component used as the binder (D) is preferably one having the viscosity of a 1% aqueous solution is from 10 to 1000 dP·s at 25° C. One with a high viscosity grade having the viscosity of a 1% aqueous solution is from 1000 to 7000 dP·s at 25° C. may be used with the above-mentioned preferably used binders in combination, and is used in an amount of preferably 30% by mass or less and more preferably 15% by mass or less of the total amount of the binder (D). For example, in a case of sodium carboxy methylcellulose, one with the degree of etherification of more than 0.6 and 1.8 or less is preferably used as the binder (D) and one with the degree of etherification of from 0.7 to 1.5 is more preferably used as the binder (D).

In addition, among the binders (D), the content of non-cellulosic binders is preferably less than 1.0% by mass and more preferably 0.5% by mass or less. Among the non-cellulosic binders, plant seed polysaccharides such as guar gum, locust bean gum, tara gum and cassia gum, plant fruit polysaccharides such as pectin and arabinogalactan, plant bark polysaccharides such as gum arabic and polysaccharides such as agar are preferably not contained or the content thereof is preferably less than 1.0% by mass, more preferably 0.5% by mass or less and even more preferably 0.1% by mass or less.

From a viewpoint of not inhibiting the fluidity of fluoride ions in water (C), the dentifrice composition of the present invention preferably does not contain natural resins such as chicle, jelutong and solver, which are used as a gum base of gums such as chewing gums and synthetic resins for gums such as polyisobutene, ester resins, poly vinyl acetate and vinyl acetate, or the content thereof is preferably 0.001% by mass or less. More preferably, the dentifrice composition does not contain them.

The dentifrice composition of the present invention preferably contains glycerin (E) Containing glycerin (E) in a certain mass ratio to water (C) enables efficient uptake into tooth enamel or dentin. From viewpoints of increasing the amount of fluoride ion uptake into tooth enamel and the like and the feeling of use, the dentifrice composition of the present invention preferably contains from 4 to 40% by mass, more preferably contains from 5 to 35% by mass and even more preferably contains from 7 to 35% by mass of glycerin (E).

From a viewpoint of increasing the amount of fluoride ion uptake into tooth enamel or dentin, the content of glycerin (E) in the dentifrice composition of the present invention is such an amount that the mass ratio (E/C) (the mass ratio to water (C)) is preferably from 3/1 to 1/3, more preferably from 1/2 to 3/1 and even more preferably from 2/3 to 3/1.

The dentifrice composition of the present invention may contain foaming agents, foaming aids, abrasives, wetting agents other than component (E), sweetening agents, preserving agents, disinfectants, medicinal component, pigments, dyes, flavors and the like as appropriate in addition to the above-mentioned components in such a range that the effects of the present invention are not impaired. It should be noted that a component which forms insoluble salts with fluoride ions is likely to inhibit the effect to promote the uptake of fluoride ions into tooth enamel and the like. Examples of the component which forms insoluble salts with fluoride ions include calcium salts such as calcium carbonate, calcium phosphate and hydroxy apatite, and the content thereof in the dentifrice composition of the present invention is preferably 2% by mass or less, more preferably 1% by mass or less and even more preferably 0.1% by mass or less. In addition, as components which form insoluble salts with fluoride ions, acids such as tribasic acids such as citric acid and ethylenediamine tetraacetate are also exemplified, and the content thereof in the composition for oral cavity of the present invention is preferably less than 0.1% by mass, more preferably less than 0.05% by mass and further preferably 0.01% by mass or less. Besides, the dentifrice composition of the present invention may be prepared, for example, in the form of gels or pastes to obtain toothpastes, gelatinous dentifrices and the like.

The dentifrice composition of the present invention has the viscosity of preferably from 500 to 10000 dPa·s and further preferably from 1000 to 7000 dPa·s at 20° C. By setting the viscosity to be 10000 dPa·s or less, the fluidity of the fluoride ion supplying compound (A) in the contained water (C) can be ensured while conferring structural viscosity on the composition by an undissolved sugar alcohol. The viscosity of the dentifrice composition can be measured by pouring the composition into a container for viscosity measurement and preserving it in a thermostat at 20° C. for 24 hours, followed by measuring the viscosity using a Helipath viscometer (B-type viscometer) under the conditions: rotor H7 (number of revolutions) 2.5 rpm, and 1 minute.

In the dentifrice composition of the present invention, when adding 25% by mass of water to 100% by mass of the composition, the viscosity (20° C.) of the resulting composition decreases to preferably 10% or less, further preferably 1 to 10%, still further preferably 3 to 8% and especially preferably 3 to 7% of the viscosity (20° C.) of the composition before water is added. Since an undissolved sugar alcohol confers structural viscosity on the composition, the dentifrice composition of the present invention exhibits a high decreasing rate of viscosity by adding water. In a preferred embodiment, the saliva dilution model during tooth brushing in which the composition is diluted with 25% of water in the mass ratio shows that the viscosity of the composition decreases to 10% or less. Therefore, high concentration of fluoride ions in water (C) is applicable to teeth with fluidity. From this viewpoint, the viscosity measured within 1 hour after adding water is used as the viscosity (20° C.) when adding 25% by mass of water.

EXAMPLES

In the following Examples, % represents % by mass.

Test Example 1

The dentifrice compositions of Examples from 1 to 7 and Comparative Examples from 1 to 6 were prepared by mixing each component in the amount shown in Table 1 for samples containing a fluoride ion supplying compound. Comparative Example 7 is a fluorine solution prepared by dissolving the fluoride supplying compound in water. Note that pH was neutral (from 6 to 8).

To the HAP pellet (APP-100 HOYA) 10 mm×10 mm×2 mm, 100 mg of each sample of the dentifrice compositions of Examples 1 to 7 and Comparative Examples 1 to 6 and the fluorine solution of Comparative Example 7 were applied for 3 minutes, the dentifrice compositions were removed using ion-exchanged water and the pellets were dried. Fluoride ions were extracted from the dried pellet for 30 seconds using 1 N hydrochloric acid and the fluorine amount adsorbed on the HAP pellet was determined using the fluoride ion electrode (ionplus-Fluoride (manufactured by ORION corporation)) and the ion analyzer (Expandable ionAnalyzer EA 940 (manufactured by ORION corporation)).

The viscosity of the samples before dilution and the viscosity of the samples after diluting 100% of the samples with 25% of purified water were measured. The measurement conditions were as follows: after preserving the samples in a thermostat at 20° C. for 1 hour, the viscosity was measured using a B-type viscometer and the rotor H7 under the conditions of (number of revolutions) 2.5 rpm and 1 minute. Provided that the viscosity of the sample after dilution was 500 dPa·s or less, the viscosity was measured using the rotor H2 under the same conditions.

TABLE 1

| Component | Example 1 | Example 2 | Example 3 | Example 4 | Example 5 | Example 5-2 | Example 6 | Example 7 | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|---|---|---|---|---|---|
| Mannitol (B) | 40 | — | 30 | 20 | 35 | 35 | 30 | 43 | — | 5 | — | 30 | 30 | — | — |
| Palatinit (B) *2 | — | 35 | — | 20 | — | — | — | — | — | — | — | — | — | — | — |
| Xylitol (F) | — | — | — | — | — | — | — | — | 40 | — | — | — | — | 55 | — |
| Sorbitol (F) | — | — | — | — | — | — | 5 | 3.5 | — | — | — | — | 10 | — | — |
| Xanthan gum | 0.5 | 0.1 | 0.2 | — | — | — | — | — | — | — | — | — | — | 15 | — |
| Sodium carboxy methylcellulose *3 | 0.5 | 0.5 | 0.5 | 0.5 | 1 | 0.8 | 1 | 0.5 | 1.5 | 1.5 | 1.5 | 1.2 | 1 | 1 | — |
| Sodium lauryl sulfate | 1 | 1 | 1 | 1 | 1 | 1 | 1 | 1 | 1 | 1 | 1 | 1 | 1 | 1.5 | — |
| Sodium fluoride | 0.21 | 0.21 | 0.21 | 0.21 | 0.21 | 0.21 | 0.21 | 0.21 | 0.21 | 0.21 | 0.21 | 0.21 | 0.21 | 0.21 | 0.21 |
| Hydrous silicic acid | 10 | 15 | 15 | 10 | 16 | 16 | 16 | 15 | 15 | 15 | 20 | 16 | 16 | — | — |
| Anhydrous silicic acid | 3 | 3 | 3 | 3 | 3 | 3 | 3 | 3 | 5 | 5 | 5 | 3 | 3 | — | — |
| Saccharin sodium | 0.05 | 0.05 | 0.05 | 0.05 | 0.05 | 0.05 | 0.05 | 0.05 | 0.05 | 0.05 | 0.05 | 0.05 | 0.05 | 0.1 | — |
| Flavor | 1 | 1 | 1 | 1 | 1 | 1 | 1 | 1 | 1 | 1 | 1 | 1 | 1 | 1 | — |
| Glycerin (E) | 24.24 | 32.14 | 29.04 | 29.24 | 26.79 | 27.94 | 17.74 | 10.24 | 21.24 | 41.24 | 31.24 | 7.54 | 7.74 | 6.19 | — |
| Purified water | 20 | 12 | 20 | 15 | 15 | 15 | 25 | 22.5 | 15 | 30 | 40 | 40 | 30 | — | 99.79 |
| Total | 100 | 100 | 100 | 100 | 100 | 100 | 100 | 100 | 100 | 100 | 100 | 100 | 100 | 100 | 100 |
| Uptake of F (μg/cm²) | 0.65 | 0.54 | 0.48 | 0.61 | 0.21 | 0.32 | 0.22 | 0.31 | 0.04 | 0.06 | 0.08 | 0.06 | 0.1 | 0.01 | 0.12 |
| Viscosity (20° C.) P1 (dPa·s) | 4150 | 3100 | 3230 | 3950 | 3790 | 3230 | 3750 | 8740 | 3250 | 2840 | 2560 | 3080 | 3620 | *1 | — |
| Viscosity (20° C.) after dilution (dPa·s) P2 | 142 | 195 | 250 | 152 | 295 | 220 | 273 | 320 | 451 | 381 | 321 | 350 | 311 | 851 | — |
| P2/P1 (%) | 3.4 | 6.3 | 7.7 | 3.8 | 7.8 | 6.8 | 7.3 | 3.7 | 13.9 | 13.4 | 12.5 | 11.4 | 8.6 | — | — |
| Water (C) | 20 | 12 | 20 | 15 | 15 | 15 | 25 | 22.5 | 15 | 30 | 40 | 40 | 30 | 6.19 | 99.79 |
| Sugar alcohol(B)/water (C) | 2 | 2.92 | 1.5 | 2.67 | 2.33 | 2.33 | 1.2 | 1.9 | 0 | 0.17 | 0 | 0.75 | 1 | 8.9 | 0 |
| Sugar alcohol component ratio (F/B) | — | — | — | — | — | — | 0.17 | 0.08 | — | — | — | — | 0.33 | 0.27 | — |
| Glycerin(E)/water (C) | 1.21 | 2.68 | 1.45 | 1.95 | 1.79 | 1.86 | 0.71 | 0.46 | 1.42 | 1.37 | 0.78 | 0.19 | 0.26 | — | — |

*1 10000 dPa·s or more
*2 Mitsui Sugar Co., Ltd.
*3 Daicel Corporation CMC1350 (the degree of etherification: from 1 to 1.5)

The dentifrice compositions of Examples 1 to 7 contain the sugar alcohol (B), which is dissolved in an amount of 5 to 30 g in 100 g of an aqueous solution at 20° C., more than water (C). As shown in Table 1, the amounts of fluorine uptake of the dentifrice compositions of Examples 1 to 7 were larger than that of a fluorine solution of Comparative Example 7. In addition, the results showed that the amounts of fluorine uptake of the dentifrice compositions of the present invention were larger than that of any dentifrice compositions of Comparative Example 1 which contains 40 g of xylitol (the solubility is 66 g in 100 g of an aqueous solution at 20° C.), Comparative Examples 2, 4 and 5 that have smaller content of the sugar alcohol (B) than water (C), Comparative Example 3 which contains no sugar alcohol (B) and Comparative Example 6 which has more than 6-fold higher content of the sugar alcohol (B) than water (C).

In addition, the dentifrice compositions of Examples 1 to 7 have larger content of the sugar alcohol (B), which is dissolved in an amount of 5 to 30 g in 100 g of an aqueous solution at 20° C., than water (C) (the mass ratio of the sugar alcohol (B)/water (C) is more than 1) and the content of the binder is 1.2% or less. Therefore, the viscosity (P2) when the dentifrice compositions of Examples 1 to 7 were diluted by adding 25% of water to 100% of the compositions at 20° C. decreased to 10% or less of the viscosity (P1) at 20° C. before dilution. It is considered that structural viscosity of the composition due to an undissolved sugar alcohol decreases by dilution. In contrast to this, the dentifrice compositions of Comparative Examples 1 to 4 have viscosity due to a binder. Therefore, the viscosity after dilution decreased to 10% or more.

What is claimed is:

1. A dentifrice composition comprising the following components (A), (B), (C) and (D):
    (A) from 0.002 to 5% by mass of a fluoride ion supplying compound in terms of fluorine,
    (B) from 25 to 65% by mass of a sugar alcohol, having a solubility of 5 to 30 g in 100 g of an aqueous solution at 20° C., wherein the sugar alcohol is one or more selected from the group consisting of mannitol, α-D-glucopyranosyl-1,6-mannitol, α-D-glucopyranosyl-1,6-sorbitol and isomalt,
    (C) from 10 to 25% by mass of water, and
    (D) from 0.1 to 1.2% by mass of a binder,
wherein the mass ratio of the component (B) to the component (C), the mass ratio (B/C), is more than 1 and 6 or less and the viscosity (20° C.) of the composition is 500 to 10000 dPa·s.

2. The dentifrice composition according to claim 1, wherein the mass ratio of the component (B) to the component (C), the mass ratio (B/C), is from 1.2 to 3.

3. The dentifrice composition according to claim 1, wherein when diluting the composition by adding 25% by mass of water in the mass ratio, the viscosity is 10% or less of the viscosity before dilution.

4. The dentifrice composition according to claim 1, wherein the fluoride ion supplying compound (A) is one or more selected from the group consisting of sodium fluoride and ammonium fluoride.

5. The dentifrice composition according to claim 1, wherein the fluoride ion supplying compound (A) is sodium fluoride.

6. The dentifrice composition according to claim 1, wherein the content of component (A) is from 0.05 to 1% by mass in terms of fluoride.

7. The dentifrice composition according to claim 1, wherein the sugar alcohol (B) is one or more selected from the group consisting of α-D glucopyranosyl-1,6-sorbitol and α-D-glucopyranosyl-1,6-mannitol.

8. The dentifrice composition according to claim 1, wherein the content of the component (B) is from 30 to 55% by mass and the mass ratio of the component (B) to the component (C), the mass ratio (B/C) is from 1.5 to 3.

9. The dentifrice composition according to claim 1, wherein the content of the component (C) is from 10 to 20% by mass.

10. The dentifrice composition according to claim 1, further comprising glycerin (E) in such an amount that the mass ratio to water (C), the mass ratio (E/C), is from 3/1 to 1/3.

11. The dentifrice composition according to claim 1, wherein (D) the binder is one or more selected from the group consisting of sodium carboxymethyl cellulose, hydroxyethyl cellulose, carboxyvinyl polymer, xanthan gum, carrageenan, sodium alginate, hydroxypropyl cellulose and sodium chondroitin sulfate.

12. The dentifrice composition according to claim 1, further comprising (F) a sugar alcohol having a solubility of more than 30 g in 100 g of an aqueous solution at 20° C., in such an amount that the mass ratio to water (C), the mass ratio (F/C), is less than 1.

13. The dentifrice composition according to claim 12, wherein component (F) is one or more selected from the group consisting of erythritol, xylitol, maltitol and sorbitol.

14. The dentifrice composition according to claim 12, wherein
    component (F) is selected from the group consisting of component (F1), (F2) and (F3), wherein:
    wherein component (F1) is a sugar alcohol having a solubility of more than 30 g and 50 g or less in 100 g of an aqueous solution at 20° C.;
    component (F2) is a sugar alcohol having the solubility of more than 50 g and 70 g or less in 100 g of an aqueous solution at 20° C.; and
    component (F3) is a sugar alcohol having a solubility of more than 70 g in 100 g of an aqueous solution at 20° C., and wherein
    the mass ratio of component (F1) to (B), the mass ratio (F1/B), is 1 or less;
    the mass ratio of component (F2) to (B), the mass ratio (F2/B), is 0.2 or less; and
    the mass ratio of component (F3) to (B), the mass ratio (F3/B), is 0.1 or less.

15. A method for promoting the uptake of fluorine into teeth, comprising applying the dentifrice composition according to claim 1 to the oral cavity.

16. The method according to claim 15, wherein the mass ratio of the component (B) to the component (C), the mass ratio (B/C), is from 1.2 to 3.

17. The method according to claim 15, wherein when diluting the composition by adding 25% by mass of water in the mass ratio, the viscosity is 10% or less of the viscosity before dilution.

18. The dentifrice composition according to claim 12, wherein the mass ratio of component (F) to component (C), the mass ratio (F/C), is less than 1.

19. The dentifrice composition according to claim 13, wherein component (F) is sorbitol.

20. A method for promoting the uptake of fluorine into teeth, comprising applying the dentifrice composition according to claim 3 into the oral cavity.

21. A method for promoting the uptake of fluorine into teeth, comprising applying the dentifrice composition according to claim 5 into the oral cavity.

22. A method for promoting the uptake of fluorine into teeth, comprising applying the dentifrice composition according to claim 7 into the oral cavity.

\* \* \* \* \*